(12) United States Patent
Williams et al.

(10) Patent No.: US 11,672,530 B2
(45) Date of Patent: Jun. 13, 2023

(54) MAGNETIC SUTURE

(71) Applicant: APPLIED MEDICAL TECHNOLOGY, INC., Brecksville, OH (US)

(72) Inventors: Derek M. Williams, Cuyahoga Falls, OH (US); Grant Wesley Phillips, Richfield, OH (US); Michelle Jackson, Uniontown, OH (US); George J. Picha, Brecksville, OH (US)

(73) Assignee: Applied Medical Technology, Inc., Brecksville, OH (US)

( * ) Notice: Subject to any disclaimer, the term of this patent is extended or adjusted under 35 U.S.C. 154(b) by 36 days.

(21) Appl. No.: 17/011,057

(22) Filed: Sep. 3, 2020

(65) Prior Publication Data

US 2021/0059667 A1    Mar. 4, 2021

Related U.S. Application Data

(60) Provisional application No. 62/895,564, filed on Sep. 4, 2019.

(51) Int. Cl.
*A61B 17/06* (2006.01)
*A61B 17/00* (2006.01)

(52) U.S. Cl.
CPC ............ *A61B 17/06166* (2013.01); *A61B 2017/00526* (2013.01); *A61B 2017/00876* (2013.01); *A61B 2017/00951* (2013.01)

(58) Field of Classification Search
CPC .... A61B 17/06166; A61B 2017/00526; A61B 2017/00876; A61B 2017/00951; A61B 2017/06171; A61B 2017/06176; A61B 2017/0618; A61B 2017/06185; A61B 2017/0619; A61B 17/06195;
(Continued)

(56) References Cited

U.S. PATENT DOCUMENTS

| 1,212,870 A * | 1/1917 | Zolper .................. A61B 17/52 |
| | | 294/65.5 |
| 10,245,021 B2 | 4/2019 | Phillips et al. |

(Continued)

FOREIGN PATENT DOCUMENTS

| WO | WO-2011025767 A1 * | 3/2011 | ....... A61B 17/06166 |
| WO | 2019/055484 A1 | 3/2019 | |

OTHER PUBLICATIONS

International Search Report and Written Opinion for corresponding International Application No. PCT/US20/49112 dated Jan. 12, 2021.
(Continued)

*Primary Examiner* — Kankindi Rwego
(74) *Attorney, Agent, or Firm* — Pearne & Gordon LLP

(57) ABSTRACT

A magnetic suture has a ferrule with a tapered region in which a knotted suture is provided and secured with an adhesive, and a straight region in which a magnet is provided. The magnetic suture can be manufactured and assembled by knotting a suture, threading it through the tapered portion, and applying adhesive. The structure and method provide a magnetic suture provide increased manufacturing tolerances and decreased failure rates, thereby reducing waste of components and time while increasing the manufacturing/assembly speed and reliability of magnetic suture assembly.

14 Claims, 2 Drawing Sheets

(58) Field of Classification Search
CPC .... A61B 17/06004; A61B 2017/06009; A61B 2017/06014; A61B 2017/06019; A61B 2017/06023; A61B 2017/06028; A61B 2017/06033; A61B 2017/06038; A61B 2017/06042; A61B 2017/06047; A61B 2017/06052; A61B 2017/06057; A61B 2017/0404; A61B 2017/0417; A61B 2017/0445; A61B 2017/045; A61B 2017/0454; B29C 66/52271; B29C 66/52272; B29C 66/52292; A61L 17/00; A61L 17/005; A61L 17/04; A61L 17/06; A61L 17/08; A61L 17/10; A61L 17/105; A61L 17/12; A61L 17/14; A61L 17/145
USPC .................................. 606/228, 224; 156/293
See application file for complete search history.

(56) References Cited

U.S. PATENT DOCUMENTS

| | | | |
|---|---|---|---|
| 2003/0105474 A1 | 6/2003 | Bonutti | |
| 2009/0224561 A1* | 9/2009 | Jackson, III | A61B 17/52 294/65.5 |
| 2011/0015653 A1* | 1/2011 | Bogart | A61B 17/06166 606/139 |
| 2015/0038976 A1 | 2/2015 | Roschak et al. | |
| 2015/0039027 A1* | 2/2015 | Broom | A61B 17/04 606/228 |
| 2016/0324517 A1 | 11/2016 | Liu | |
| 2017/0049439 A1* | 2/2017 | Keyser | A61B 17/0469 |
| 2018/0049733 A1* | 2/2018 | Zhao | A61B 17/06166 |
| 2019/0076141 A1 | 3/2019 | Liu | |
| 2019/0133591 A1* | 5/2019 | Dobashi | A61B 17/06166 |
| 2020/0360017 A1 | 11/2020 | Liu | |

OTHER PUBLICATIONS

International Preliminary Report on Patentability for corresponding International Application No. PCT/US2020/049112 dated Mar. 8, 2022.
Extended European Search Report dated Oct. 6, 2022 for corresponding European Application No. 208618009.9.

* cited by examiner

MAGNETIC SUTURE

CROSS-REFERENCE TO RELATED APPLICATION

This application claims priority to U.S. Provisional Application Ser. No. 62/895,564, filed on Sep. 4, 2019, the entirety of which is incorporated herein by reference.

BACKGROUND

The present disclosure relates to a magnetic suture. More particularly, the disclosure relates to a suture having a magnet at one end (a magnetic tip). Such a magnetic suture may be used, for example, in a magnetic U-stich device, like that described in U.S. Pat. No. 10,245,021, entitled "MAGNETIC U-STITCH DEVICE" and issued on Apr. 2, 2019, the entirety of which is herein incorporated by reference.

As described in the '021 patent, a suture having a magnetic tip is inserted into a body cavity of a patient (to be withdrawn by a magnetic probe of opposite polarity) via a hypodermic needle. In some embodiments, the suture and magnetic tip are advanced in the hypodermic needle via a cannula, where the magnet of the magnetic tip has a diameter greater than an inner diameter of the cannula. Therefore, an insertion force on the cannula into the hypodermic needle is transferred to the magnet, and thus to the suture that is also in the hypodermic needle. Put another way, inserting the suture having a magnetic tip can impart a force on the magnetic tip and away from the suture itself.

As seen in FIG. 1, according to a current design of a magnetic suture, the magnetic suture 100 includes a small cylindrical magnet 102, a thin tubular stainless steel sleeve (hereinafter, the "ferrule") 104, a suture 106 having a knot 108 at one end, and room-temperature curing adhesive 110 for holding the suture 106/knot 108, magnet 102, and ferrule 104 together. The ferrule 104 may be a laser cut stainless steel hypodermic tube having a constant inner diameter and outer diameter. The magnet 102 is flush at one end with the end of the ferrule 104, and the adhesive 110 secures the suture 106/knot 108, magnet 102, and ferrule 104 together at the other end.

Considering this, some designs of magnetic sutures can suffer failure by detachment of the magnet from the suture with only small amounts of tension during use and testing (e.g., during insertion described above). Further, manufacturing and assembly techniques for attaching a magnet to the end of a suture can suffer from a number of deficiencies. For example, manufacturing tolerances can be small, making assembly and production on a mass scale difficult. Additionally, errors in the alignment of the magnet relative to the suture can affect functionality of suturing devices. For example, an off-center or angled magnet may not fit within a hypodermic needle and/or may not be able to be advanced through the needle.

BRIEF SUMMARY

According to one example of the present disclosure, a magnetic suture comprises: a ferrule having a small opening at an end of a tapered region, and having a large opening at an end of a straight region, wherein the small opening is at an opposite end of the ferrule than the large opening and at least a portion of the tapered region has an inner diameter that is tapered toward the small opening; a suture extending from the small opening; and a magnet at least partially within the straight region.

In various embodiments of the above example, the suture is knotted and the knot is located within the tapered region, between the magnet and the small opening; the magnetic suture further comprises an adhesive within the tapered region, between the magnet and the small opening; an inner diameter of the straight region is substantially constant and is substantial equal to an outer diameter of the magnet; an inner diameter of the small opening is substantially equal to a diameter of the suture; and/or the magnet extends from the large opening.

According to another example of the present disclosure, a method comprises knotting a suture at a first end of the suture; threading a second non-knotted end of the suture through a small opening of a ferrule, such that the knot is in an interior of the ferrule; applying adhesive to an interior of the ferrule; and inserting a magnet into a large opening of the ferrule, wherein: the small opening is at an opposite end of the ferrule than the large opening, and the knot is between the magnet and the small opening.

In various examples of the above embodiment, the method further comprises: prior to threading the second non-knotted end of the suture through the small opening of the ferrule, cutting a portion of remaining strand of the suture beyond the knot at the first end; the threading is performed by vacuum tooling; the threading comprises: with a vacuum tool, picking up the ferrule and centering the ferrule with respect to a vacuum applied by the vacuum tool, and with the vacuum tool, sucking the second non-knotted end of the suture through the small opening of the ferrule, such that the knot is in an interior of the ferrule; the method further comprises: cleaning excess adhesive that escapes through the small opening of the ferrule; the small opening of the ferrule opens to a tapered region of the ferrule, the large opening of the ferrule opens to a straight region of the ferrule, the suture extends from the small opening, and the magnet is at least partially within the straight region; and/or the magnet extends from the large opening.

DETAILED DESCRIPTION

A magnetic suture and its manufacturing method according to the present disclosure overcome the above-discussed deficiencies, thereby reducing waste of components and time while increasing the speed and reliability of magnetic suture assembly.

Figure 2:
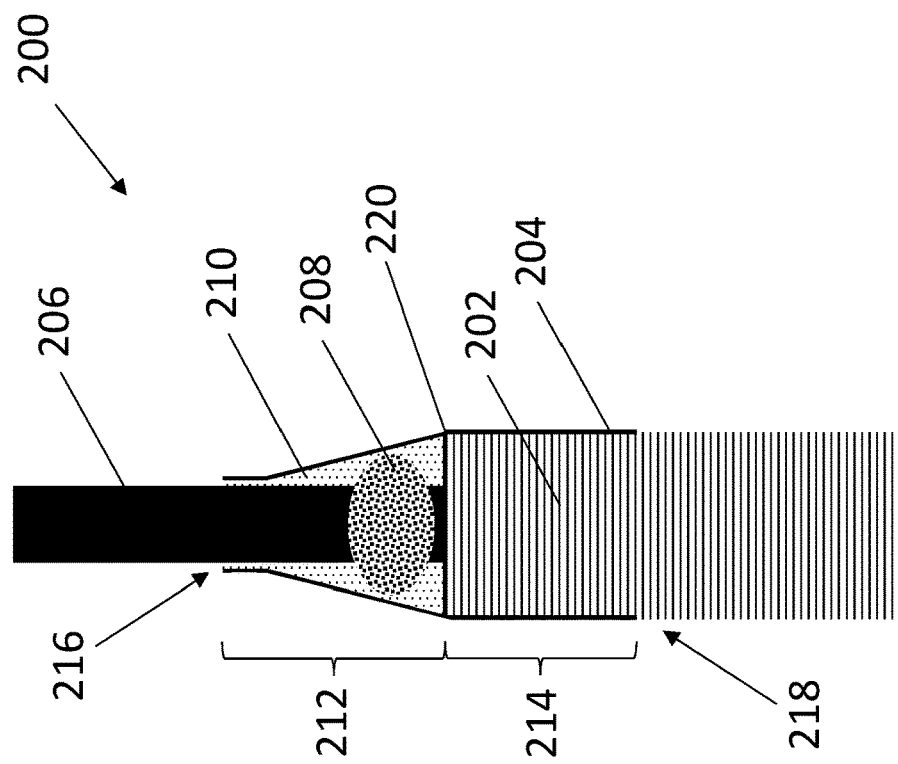
FIG. 2 illustrates an example suture having a magnetic tip according to the present disclosure.
Figure 1:
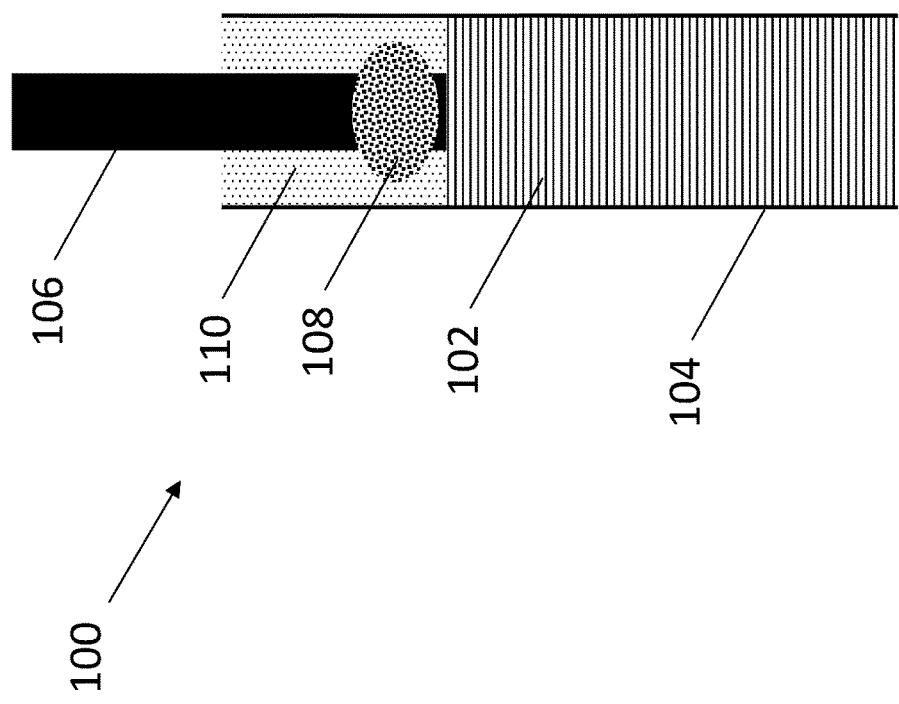
FIG. 1 illustrates an example suture having a magnetic tip according to an existing design.

As seen in FIG. 2, a magnetic suture 200 of the present disclosure has a ferrule 204 with a tapered region 212 in continuity with or adjacent to a straight region 214. In particular, the ferrule 204 has a tapered region (also referred to herein as a "transition region") 212 where at least the inner diameter decreases (variably or continuously), and that opens, to a smaller opening 216; and a straight region 214 preferably having a substantially constant inner diameter that opens to a larger opening 218. The tapered region 212 may only be tapered for a portion of its length between the small opening 216 and the straight region 214 but may be tapered at a continuous or variable degree for an entirety of the region 212. Preferably the small opening 216 is only slightly larger than, or substantially equal to, the outer diameter of the suture 206; and the straight region 214 has an inner diameter that is slightly larger than, or substantially equal to, the outer diameter of a cylindrical magnet 202 therein. The ferrule 204 does not need to extend the length of the magnet and thus the large opening 218 does not need to be flush with the end of the magnet 202. In other words, the magnet 202 may extend out of the large opening 218.

At the other end of the straight region 214 (opposite the large opening 218), the ferrule 204 has a natural "stop" or shoulder 220 where the inner diameter of the ferrule 204 begins to transition/decrease in the transition region 212. The magnet 202 cannot be inserted beyond the shoulder 220 into the transition region 212 of the ferrule 204 because the inner diameter of the ferrule 204 is less than the outer diameter of the magnet 202. Although the shoulder is naturally created by the shape of the ferrule 204, the ferrule may also include a physical stop (such as a shelf) extending perpendicular to the sides of the ferrule in the straight region 214 at the shoulder.

Additionally, the suture 206 is knotted, with the knot 208 located within the transition region 212 of the ferrule 204. The ferrule 204, suture 206, and magnet 202 can be held together via adhesive 210 within the transition region 212.

According to this structure, because the tapered ferrule 204 creates a mechanical stop for the suture knot 208 at the small opening 216, and the magnet 202 and adhesive 210 are forced against the knot 208, extra suture 206 can be accommodated in the ferrule 204. This lessens the risk of the suture unraveling under tension. Further, the knot 208 and ferrule 204 create a natural mechanical joint as a fail-safe even if the adhesive 210 fails.

Still further, the tapered region 212 of the ferrule 204 helps ensure that the suture is straight and centered relative to the ferrule 204 and magnet 202, thus preventing the above-noted crooked assemblies. The tapered region 212 of the ferrule also permits movement of the suture 206 while the adhesive 210 cures because the position of the suture 206 is guided by the shape of the tapered region 212 of the ferrule 204 and the position of the magnet 202 therein. In other words, the knot 208 of the suture is sandwiched between the magnet 202 and the small opening 216 of the ferrule 204, thereby increasing the strength of adhesion between the elements of the magnetic suture 200 and helping to ensure proper position of the knot 208 and suture 206 within the transition region 212 during curing of the adhesive.

Figure 3:
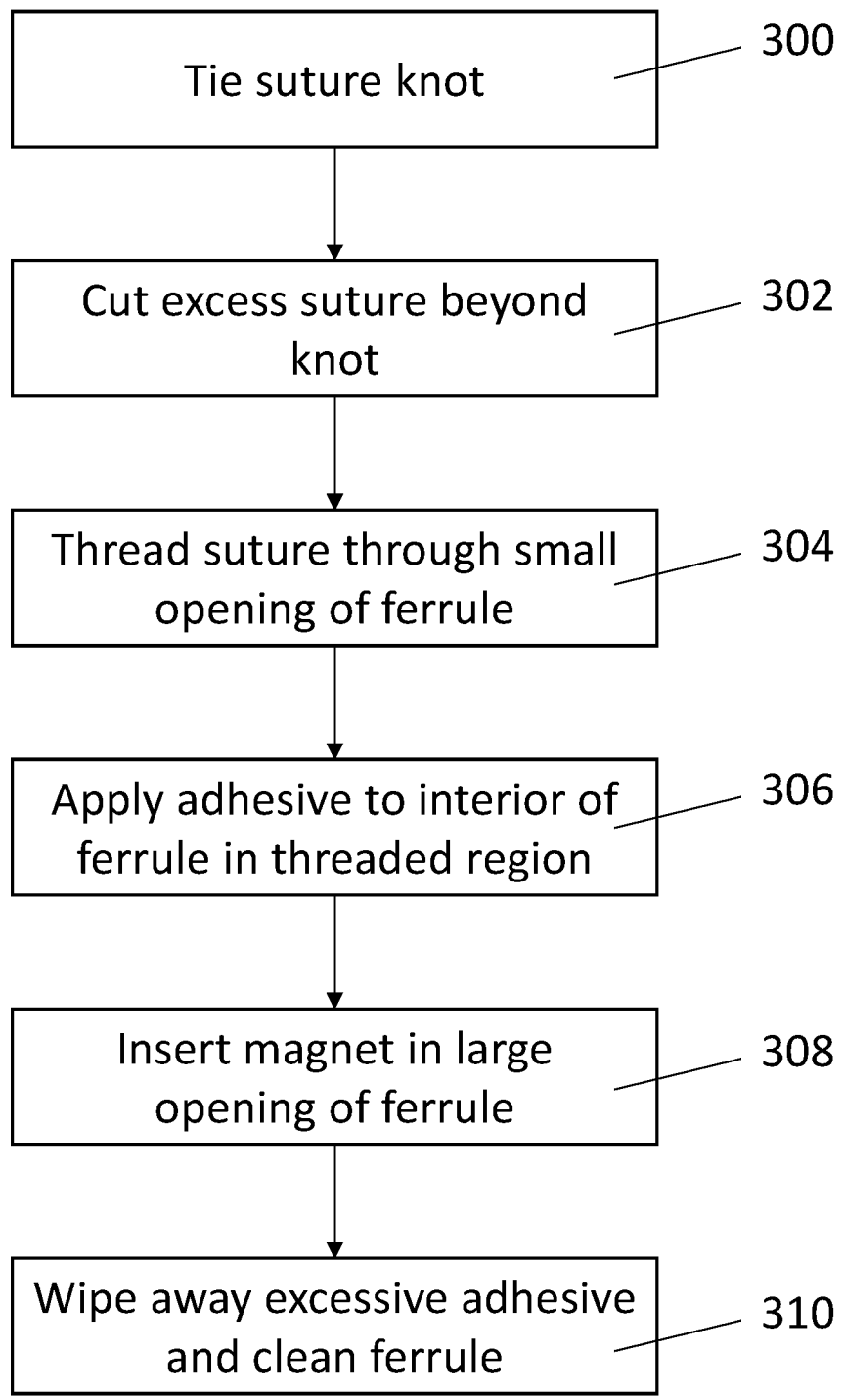
FIG. 3 illustrates a method of manufacturing a suture having a magnetic tip according to the present disclosure.

The magnetic suture 200 of FIG. 2 can be manufactured and assembled according to the method illustrated in FIG. 3. As seen therein, the method begins by tying a knot 300 near one end of a suture. Next, the small remaining strand of the suture beyond the knot is cut 302 in a manner that does not damage the knot itself. It is not necessary to cut as close to the knot as possible. Thus, the magnetic suture may be manufactured with greater tolerance relative to current designs and any potential damage to the knot from the cut is minimized.

After the knot is formed, the non-knotted end of the suture is threaded 304 through the small opening of the ferrule from the large opening side of the ferrule. The knot of the suture is too large to go through the small opening of the ferrule, and therefore hits a consistent mechanical stop when the suture is threaded or otherwise pulled through the small opening. In some embodiments, this can be accomplished using vacuum tooling. For example, the ferrule can be picked up and centered at the end of the vacuum tooling (due to the shoulder created by the tapered end of the ferrule), and the non-knotted end of the suture can be sucked through the small opening of the ferrule with an applied vacuum such that the vacuum essentially threads the ferrule with the knot in the tapered region. Using a vacuum can reduce reliance on a steady hand and keen eye of a person doing the assembly.

Following threading, a drop of adhesive is applied 306 to the interior of the ferrule. It is not necessary to place this drop deep inside of the ferrule as in some current techniques. Further, because the magnet is placed into the ferrule after the application of adhesive (see below), the total amount of adhesive may be applied in a single (relatively larger) drop than that used for some existing designs, and can be placed anywhere along the interior of the ferrule. This also permits the use of a more viscous adhesive because application of the magnet, rather than the adhesive's viscosity and gravity, causes the adhesive to spread. Still further, because excess adhesive can ooze from the small opening of the ferrule and be wiped away (see below), the amount of adhesive applied is subject to greater tolerances. This all can simplify and ease the manufacturing and assembly process.

The magnet (in the correct polarity orientation) is then inserted 308 into the large opening of the ferrule as far as possible until it hits the natural stop/shoulder inside the ferrule. Inserting the magnet after applying the adhesive causes the magnet to act as a piston that pushes the adhesive throughout the inside of the ferrule and around the knot and magnet, thereby helping to ensure appropriate adhesive coverage.

Finally, any adhesive that escapes through the small opening of the ferrule can be wiped away and cleaned 310 from the ferrule.

Quality checks of the above-described magnetic suture can be performed by simply tugging on the suture at one end, and the magnet at the other end, to assure they are securely attached to the ferrule. For the reasons noted above, this process does not damage the final assembly.

What we claim is:

1. A magnetic suture comprising:
   a ferrule having a small opening at an end of a transition region, and having a large opening at an end of a straight region, wherein the small opening is at an opposite end of the ferrule than the large opening and a portion of the transition region has an inner diameter that is tapered toward the small opening, wherein a portion of the transition region at the end of the small opening has a constant inner diameter;
   a suture extending from the small opening, wherein an inner diameter of the small opening is substantially equal to a diameter of the suture; and
   a magnet at least partially within the straight region, wherein at the end of the straight region and opposite the large opening, the ferrule has a shoulder where the inner diameter of the ferrule begins to decrease in the transition region and the shoulder prevents the magnet from being inserted into the transition region.

2. The magnetic suture of claim 1, further comprising an adhesive within the transition region, between the magnet and the small opening.

3. The magnetic suture of claim 1, wherein an inner diameter of the straight region is substantially constant and is substantially equal to an outer diameter of the magnet.

4. The magnetic suture of claim 1, wherein the magnet extends from the large opening of the straight region.

5. The magnetic suture of claim 1, wherein the ferrule accommodates extra suture in the transition region which lessens the risk of the suture unraveling under tension when the suture is being tugged on from the small opening.

6. The magnetic suture of claim 1, wherein the suture is knotted to form a suture knot that is larger than the small opening to prevent the suture knot from going through the small opening, and the suture knot is located within the transition region, between the magnet and the small opening, wherein the small opening at the end of the transition region creates a mechanical stop for the suture knot.

7. The magnetic suture of claim 6, wherein the suture knot and the ferrule create a natural mechanical joint as a fail-safe for the magnet.

8. A method for the magnetic suture of claim 1 comprising:
   providing the ferrule having the small opening at the end of the transition region, and having the large opening at the end of the straight region, wherein the small opening is at the opposite end of the ferrule than the large opening and the portion of the transition region has the inner diameter that is tapered toward the small opening, wherein the portion of the transition region at the end of the small opening has the constant inner diameter;
   providing the suture extending from the small opening, wherein the inner diameter of the small opening is substantially equal to the diameter of the suture; and
   providing the magnet at least partially within the straight region,
   wherein at the end of the straight region and opposite the large opening, the ferrule has the shoulder where the inner diameter of the ferrule begins to decrease in the transition region and the shoulder prevents the magnet from being inserted into the transition region.

9. The method of claim 8, further comprising providing the adhesive within the transition region, between the magnet and the small opening.

10. The method of claim 8, wherein an inner diameter of the straight region is substantially constant and is substantially equal to the outer diameter of the magnet.

11. The method of claim 8, wherein the magnet extends from the large opening of the straight region.

12. The method of claim 8, wherein the ferrule accommodates extra suture in the transition region which lessens the risk of the suture unraveling under tension when the suture is being tugged on from the small opening.

13. The method of claim 8, wherein the suture is knotted to form the suture knot that is larger than the small opening to prevent the suture knot from going through the small opening, and the suture knot is located within the transition region, between the magnet and the small opening, wherein the small opening at the end of the transition region creates the mechanical stop for the suture knot.

14. The method of claim 13, wherein the suture knot and the ferrule create a natural mechanical joint as a fail-safe for the magnet.

\* \* \* \* \*